United States Patent [19]

Lee et al.

[11] Patent Number: 4,496,732
[45] Date of Patent: Jan. 29, 1985

[54] STEREOSELECTIVE REDUCTION OF 2- OR 3-SUBSTITUTED 4-PIPERIDONES WITH SODIUM BOROHYDRIDE

[75] Inventors: George E. Lee, Somerville; Thomas B. K. Lee, Whitehouse Station, both of N.J.

[73] Assignee: Hoechst-Roussel Pharmaceuticals Inc., Somerville, N.J.

[21] Appl. No.: 474,856

[22] Filed: Mar. 14, 1983

[51] Int. Cl.$^3$ ............................................. C07D 211/46
[52] U.S. Cl. ...................................... 546/216; 546/242
[58] Field of Search ................................ 546/216, 242

[56] References Cited

U.S. PATENT DOCUMENTS

| | | | |
|---|---|---|---|
| 4,216,218 | 8/1980 | Klioze et al. | 424/267 |
| 4,302,590 | 11/1981 | Klioze et al. | 546/216 |
| 4,312,876 | 1/1982 | Klioze et al. | 424/267 |

OTHER PUBLICATIONS

D. R. Howton, Jour. Org. Chemistry, vol. 10, (1945), pp. 277–282.
J. A. Waters, Jour. Med. Chem., (1978), vol. 21, No. 7, pp. 628–633.
Tetsuji Kametani et al., Heterocycles, vol. 14, (1980), No. 6, pp. 775–778.
Tetsuji Kametani et al., CA 95: 132587t.
Kametani, Yakugaku Zasshi, 1981, 101(5), pp. 421–430.
H. O. House, "Modern Synthetic Reactions", W. A. Benjamin, Inc., N.Y., (1965), pp. 23–33.
Cram et al., J. Amer. Chem. Soc., 81, (1959), pp. 2748–2755.
Karabatsos, J. Amer. Chem. Soc., 89, (1967), pp. 1367–1371.
Kametani et al., Yakugaku Zasshi, 100, (1980), pp. 839–843.
Kametani et al., Yakugaku Zasshi, 100(8), (1980), pp. 844–854.
Schaeffer et al., J. Amer. Chem. Soc., 71, (1940), pp. 2143–2145.
Matsumoto et al., J. Org. Chem., 27, (1969), pp. 79–84.

Primary Examiner—Norma S. Milestone
Attorney, Agent, or Firm—Tatsuya Ikeda

[57] ABSTRACT

A stereoselective reduction of 2- or 3-substituted 4-piperidones of the formula

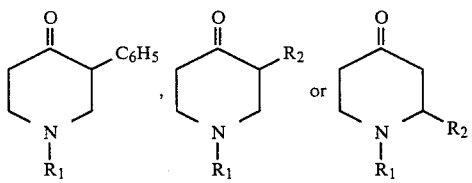

where $R_1$ is hydrogen, loweralkyl or benzyl and $R_2$ is methyl or ethyl, to the di-equatorial isomer of the corresponding 4-piperidinol is described. Said reduction is conducted by use of sodium borohydride in a protic solvent medium at a temperature substantially lower than ambient temperature in the presence of an effective amount of an inorganic acid. Under favorable reaction conditions, the stereoselectivity of the reduction is so high that simple crystallization of the reaction product affords the pure isomer in a commercially acceptable and advantageous process.

20 Claims, No Drawings

STEREOSELECTIVE REDUCTION OF 2- OR 3-SUBSTITUTED 4-PIPERIDONES WITH SODIUM BOROHYDRIDE

This invention relates to a stereoselective reduction of 2- or 3-substituted 4-piperidones of the formula I, II or III,

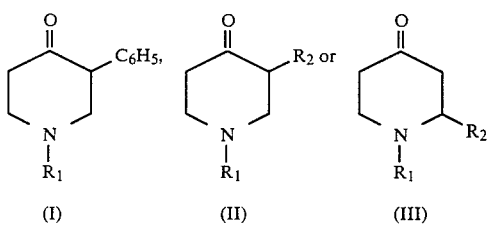

where $R_1$ is hydrogen, loweralkyl or benzyl and $R_2$ is methyl or ethyl, to the di-equatorial isomer of the corresponding 4-piperidinol of the formula IV, V or VI. Said reduction is conducted by use of sodium borohydride in a protic solvent medium at a temperature substantially lower than ambient temperature in the presence of an effective amount of an inorganic acid. Under favorable reaction conditions, the stereoselectivity of the reduction is so high that simple crystallization of the reaction product affords the pure isomer in a commercially acceptable and advantageous process.

The di-equatorial isomers of the compounds IV, V and VI obtained by this invention are dipicted by the formula IVa, Va, and VIa, respectively. As can be seen from the formula, the di-equatorial isomers of the 3,4-substituted compounds, namely, compounds IVa and Va, are trans isomers with respect to the 3- and the 4-substituents, whereas the di-equatorial isomers of the 2,4-substituted compounds, namely, compounds VIa, are cis isomers with respect to the 2- and the 4-substituents.

The compounds IV are useful for synthesizing compounds of the formula VII by reacting them with substituted fluorobenzenes, the substituent being hydrogen, loweralkyl, loweralkoxy, halogen, hydroxy, nitro, amino, acetamido, trifluoromethyl, benzyloxy, loweralkanoyloxy, or cyano. The term "lower" as used in this specification and the appended claims shall mean up to 6 carbon atoms. Said reaction can conveniently be conducted, for instance, by combining compound VII with NaH in DMF, and at the end of hydrogen gas evolution adding thereto a substituted fluorobenzene as described in Klioze et al U.S. Pat. Nos. 4,216,218, 4,302,590 and 4,312,876. This reaction is not accompanied by any appreciable scrambling of the stereo orientation of the 3- or 4-substituent. The compounds of the formula VII, are useful as antidepressants and analgesic agents as described in said U.S. Pat. Nos. 4,216,218, 4,302,590 and 4,312,876.

The compounds V and VI can be reacted to afford compounds of formula VIII and IX, respectively, where Ar is a phenyl or substituted phenyl group.

The compounds VIII and IX, in general, are believed to possess analgetic activities. For instance, an article entitled "Aromatic Esters of Nonquaternary Carbon-4 Piperidinols as Analgesics" by James A. Waters, Journal of Medicinal Chemistry, Vol 21, No. 7 (1978), pp. 628–633, describes the preparation and the analgesic activities of various aromatic carboxylic esters of 1-methyl-4-piperidinol compounds having a general formula VIII; where Ar is phenyl or substituted phenyl, the substituent being loweralkyl, loweralkoxy or flourine; $R_4$ is hydrogen, methyl or carboethoxy; and $R_5$ is methyl or β-phenylethyl. It is particularly interesting to note that some cis and trans forms of the compound of the formula VIII are stated therein to have quite different analgetic activities.

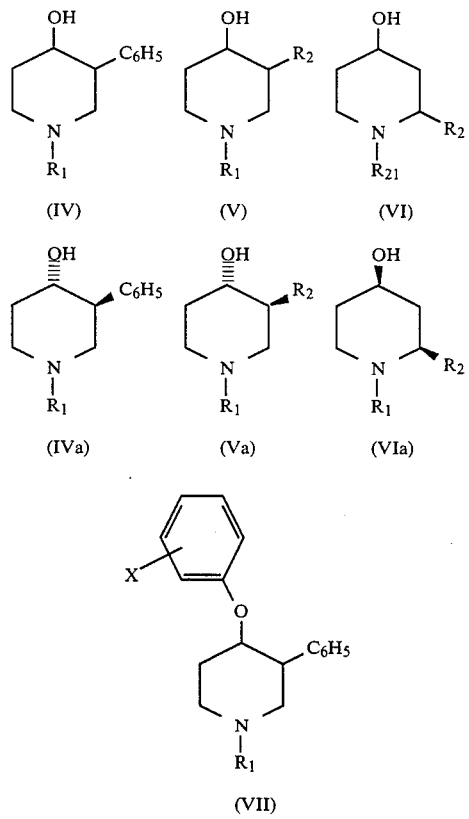

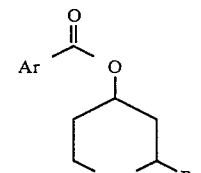

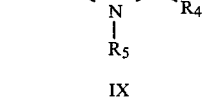

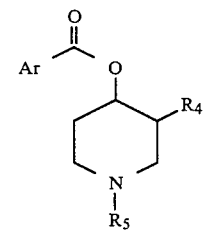

Since two stereo isomers of a given 4-piperidinol compound of the formula IV, V or VI often give rise to different pharmaceutical activities of end products derived therefrom such as compounds of the formula VII, VIII or IX and since the end products derived from the di-equatorial isomers often have better pharmaceutical activities, it is important to develop a process for a stereoselective reduction of the 4-piperidone compounds of the formula I, II or III to the di-equatorial isomers of the corresponding piperidinol compounds of the formula IV, V or VI.

It has now been discovered that when reduction of the compound I, II or III is conducted by use of sodium borohydride in a protic solvent at a temperature substantially lower than ambient temperature in the presence of an inorganic acid, the stereoselectivity of the reduction to the di-equatorial isomer product is very high so that frequently a simple crystallization of the reaction product conducted in a commercially acceptable and advantageous manner affords the di-equatorial isomer in a substantially pure form. The stereoselectivity obtained by this invention is higher than those obtained by other methods such as dissolving metal reduction (eg. Na in $NH_3$), reduction with $B_2H_6$, reduction with aluminum isopropoxide, or catalytic reduction using, for instance, a platinum, palladium or rhodium catalyst, or reduction with $NaBH_4/ROH$.

The method of this invention has a further advantage that when the starting 4-piperidone compound is a 3-phenyl-4-piperidone (namely, compound I), the reduction of the carbonyl group to the hydroxyl group is not accompanied by undesirable reduction of the phenyl group to any appreciable extent, which is in contrast to dissolving metal reduction methods where such side reaction often occurs to a substantial extent.

In depicting the stereo orientations of 2-, 3- or 4-substituent of the piperidine ring, heavy solid lines ( ◂ ) indicate the substituent is above the average plane of the piperidine ring and broken lines (---) indicate the substituent is below the average plane of the piperidine ring. A light solid line (——) indicates the substituent may be above or below the average plane of the piperidine ring.

The stereoselective reduction of this invention is conducted in a protic solvent medium. Preferably, the protic solvent medium comprises an alcohol, water or a mixture thereof. A preferred example of the alcohol is methanol. The choice of the composition of the solvent medium depends upon, among other things, the solubility of the reactant and the product in the solvent medium and the reaction temperature selected. For instance, where a reaction temperature of below 0° C. is desired, pure water medium may be unsuitable and hence some other reaction medium such as a mixture of water and methanol, pure methanol or a mixture of tetrahydrofuran and water can be used. It has been found that generally speaking, polar solvents are preferred. Examples of preferred solvent medium include mixtures of water and methanol, for instance, in a volume ratio of 10:3 or 7:3, and mixtures of tetrahydrofuran and water, for instance, in a volume ratio of 9:1.

It has been discovered that the presence of an inorganic acid in the reaction medium further enhances the stereoselectivity of the reduction. Examples of inorganic acids suitable for this invention include hydrochloric acid, hydrobromic acid, sulfuric acid, boric acid, phosphoric acid and mixtures and acid salts thereof. Generally speaking, the stereoselectivity increases with the concentration of the inorganic acid. Thus, it is preferable that the molar amount of the inorganic acid be at least one-half the molar amount of the starting 4-piperidone compound. It is more preferable to have at least a molar equivalent of the inorganic acid. The term "molar amount of the inorganic acid" as used in the specification and the appended claims shall mean the molar amount of acidic hydrogen of the acid molecule, rather than the molar amount of the acid molecule itself. As the concentration of the inorganic acid in the reaction system becomes substantially higher than the equi-molar concentration with respect to the ketone, the consumption of sodium borohydride through hydrolysis reaction tends to become more appreciable.

It has been found that in order to achieve a high stereoselectivity of the reduction it is preferable to conduct the reduction at a temperature substantially lower than the ambient temperature. Thus, it is preferable to conduct the reduction at a temperature lower than about 0° C. It has been observed that the stereoselectivity increases with the decrease of the reaction temperature. Thus it is more preferable to conduct the reaction at low temperatures, for instance, in the range of from about −30° C. to about −10° C. The consumption of sodium borohydride through hydrolysis increases with the reaction temperature. It has been observed that very little hydrolysis of sodium borohydride occurs when the temperature is below −10° C.

When the reaction condition is judiciously chosen by adjusting the reaction temperature, composition of the solvent medium and the concentration of the inorganic acid relative to that of the starting 4-piperidone compound, the stereoselectivity of the reduction is often so high that simple crystallization of the reaction product affords the isomer in a substantially pure form. Quite often this is a significant commerical advantage. For example, when N-methyl-3-phenyl-4-piperidone is reduced with sodium borohydride at −15° C. in 7:3 mixture of water and methanol in the presence of a molar equivalent of HCl with respect to the ketone, about 96% yield of the trans (diequatorial) isomer of the corresponding 4-piperidinol can be obtained.

The starting 3-phenyl-4-piperidone compounds (I) can be obtained according to the method disclosed in the afore-mentioned U.S. Patents. The piperidone compounds II and III can be prepared by methods known in the art, for instance, by making use of the method described by Howton, J. Org. Chem. Vol. 10, 277 (1945).

The following examples summarize the stereoselectivities of reductions conducted under various conditions.

EXAMPLE I

N-methyl-3-phenyl-4-piperidone was reduced with sodium borohydride under various reaction conditions. The results are summarized in Table 1.

TABLE 1

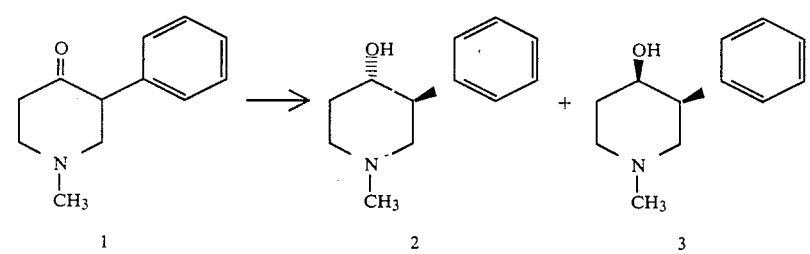

| 1 mmol | REDUCING AGENT | mmol | SOLVENT | TEMP °C. | 2/3 | REMARKS |
|---|---|---|---|---|---|---|
| 2.6 | $NaBH_4$ | 13.0 | MeOH | −5 | 73/27 | |
| 2.6 | $NaBH_4$ | 13.0 | MeOH | −20 | 85/15 | |
| 2.6 | $NaBH_4$ | 13.0 | MeOH | −60 | 86/14 | |
| 2.6 | $NaBH_4$ | 13.0 | $H_2O$ 9, MeOH 1 | −5 | 81/19 | |
| 2.6 | $NaBH_4$ | 13.0 | $H_2O$ 8, MeOH 2 | −10 | 85/15 | |
| 5 | $NaBH_4$ | 2.5 | $H_2O$ 7, MeOH 3 | −15 | 88/12 | CONTROL-NO ACID |
| 5 | $NaBH_4$ | 2.5 | $H_2O$ 7, MeOH 3 | −15 | 91/9 | 1.25 mmol HCl pH 7.2 |
| 5 | $NaBH_4$ | 2.5 | $H_2O$ 7, MeOH 3 | −15 | 93.5/6.5 | 2.5 mmol HCl pH 6.4 |
| 5 | $NaBH_4$ | 2.5 | $H_2O$ 7, MeOH 3 | −15 | 96/4 | 5 mmol HCl pH 1.2 |
| 2.6 | $NaBH_4$ | 2.6 | $H_2O$ 10, MeOH 3 | −10 | 81/19 | CONTROL-NO ACID |
| 2.6 | $NaBH_4$ | 2.6 | $H_2O$ 10, MeOH 3 | −10 | 94/6 | $H_3BO_3$ 10 mmol |
| 5.3 | $NaBH_4$ | 2.6 | $H_2O$ 10, MeOH 3 | −10 | 97/3 | $H_3PO_4$ 3 mmol |
| 2.6 | $NaBH_4$ | 18.0 | $H_2O$ 10, MeOH 3 | −10 | 93/7 | $ZnCl_2$ 6.6 mmol pH 8.0 |

EXAMPLE II

N-methyl-3-phenyl-4-piperidone was reduced (1) by dissolving metal method using Li, Na, and K and (2) by using aluminum isopropoxide and lithium isopropoxide. The results are summarized in Table 2. The results of Table 1 should be compared with those of Table 2 as an indication of the improved stereoselectivity of the instant invention.

TABLE 2

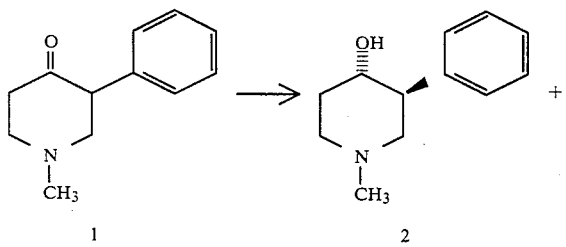

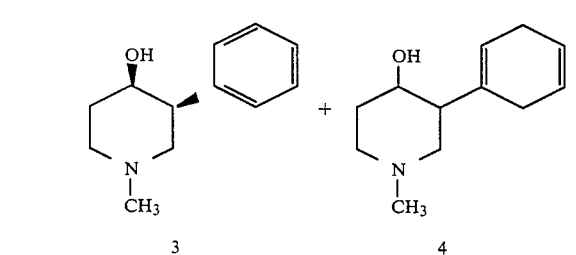

| REDUCING AGENT | SOLVENT | TEMP °C. | 2 | 3 | 4 | |
|---|---|---|---|---|---|---|
| $Al(i-PrOH)_3$ | i-PrOH | 82 | 13 | 87 | | |
| Li i-PrOH | i-PrOH | 82 | 30 | 70 | | |
| Na | $NH_3$/EtOH | −38 | 8 | — | — | 1.5 eq Na |
| Na | $NH_3$/EtOH | −38 | — | — | 100% | 6 eq Na |
| Li | $NH_3$/EtOH | −38 | — | — | 100% | 19 eq Li |
| Na | n-BuOH | 65 | 63 | 37 | | |
| Na | i-PrOH | 65 | 50 | 50 | | |
| Li | i-PrOH | 65 | 17 | 82 | | |

TABLE 2-continued

| K | n-BuOH | 65 | 76 | 24 |
|---|---|---|---|---|

EXAMPLE III

N-methyl-3-phenyl-4-piperidone was reduced by a catalytic hydrogenation method using platinum, palladium and rhodium. The results are summarized in Table 3. The results of Table 1 should be compared with those of Table 3 as an indication of the improved stereoselectivity of the instant invention.

TABLE 3

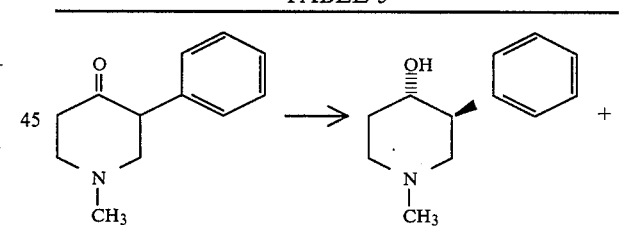

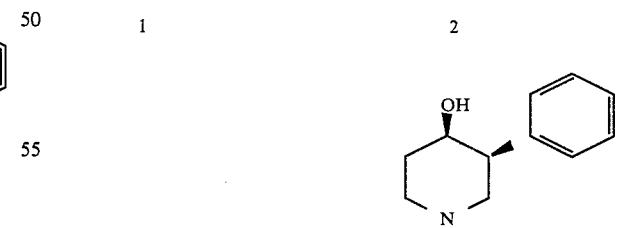

| Cat | SOLV | $H_2$(psi) | 2 | 3 |
|---|---|---|---|---|
| $PtO_2$ | HOAc | 55 | 60 | 40 |
| $PtO_2$ | HOAc + HCl | 55 | 54 | 46 |
| $PtO_2$ | MeOH | 35 | 70 | 30 |
| 10% Pd/C | MeOH | 35 | N.R. | |
| 5% Rh/C | MeOH | 30 | 33 | 67 |

EXAMPLE IV

N-methyl-3-methyl-4-piperidone was reduced with sodium borohydride. For the sake of comparison, it was also catalytically hydrogenated using platinum oxide catalyst. The results are summarized in Table 4. They illustrate the stereoselectivity of the instant process.

TABLE 4

[Reaction scheme: N-methyl-3-methyl-4-piperidone (1) → cis 4-piperidinol (2) + trans 4-piperidinol (3)]

| 1 mmol | REDUCING AGENT | mmol | SOLVENT | TEMP °C. | 2/3 | REMARKS |
|---|---|---|---|---|---|---|
| 10 | PtO$_2$/H$_2$ | 1 | MeOH | 23 | 0/100 | H$_2$ = 1 Atm |
| 10 | PtO$_2$/H$_2$ | 1 | MeOH | 23 | 25/75 | H$_2$ = 50 psi |
| 5 | NaBH$_4$ | 10 | MeOH | 23–35 | 75/25 | |
| 5 | NaBH$_4$ | 10 | MeOH | −10 | 79/21 | |
| 5 | NaBH$_4$ | 2.5 | H$_2$O 7, MeOH 3 | −10 | 84/16 | |
| 5 | NaBH$_4$ | 2.5 | H$_2$O 7, MeOH 3 | −10 | 92/8 | 2.5 mmol H$_3$PO$_4$ |
| 2.5 | NaBH$_4$ | 2.5 | H$_2$O 7, MeOH 3 | −10 | 93/7 | 2.5 mmol H$_3$PO$_4$ |
| 5 | NaBH$_4$ | 2.5 | H$_2$O | 0–2 | 84/16 | pH 12.5 |
| 5 | NaBH$_4$ | 2.5 | H$_2$O | 0–2 | 87/13 | 1.25 mmol HCl pH 8.1 |
| 5 | NaBH$_4$ | 2.5 | H$_2$O | 0–2 | 88/12 | 2.5 mmol HCl pH 7.9 |
| 5 | NaBH$_4$ | 2.5 | H$_2$O | 0–2 | 91/9 | 5 mmol HCl pH 1.5 |

EXAMPLE V

N-methyl-2-methyl-4-piperidone was reduced with sodium borohydride. For the sake of comparison, it was also catalytically hydrogenated using platinum oxide catalyst. The results are summarized in Table 5.

TABLE 5

[Reaction scheme: N-methyl-2-methyl-4-piperidone (1) → 4-piperidinol isomer (2) + 4-piperidinol isomer (3)]

| 1 mmol | REDUCING AGENT | mmol | SOLVENT | TEMP °C. | 2/3 | REMARKS |
|---|---|---|---|---|---|---|
| 10 | PtO$_2$/H$_2$ | 1 | HOAc | 23 | 87.5/12.5 | H$_2$ = 45 psi |
| 10 | PtO$_2$/H$_2$ | 1 | MeOH | 23 | 77/23 | H$_2$ = 45 psi |
| 5 | NaBH$_4$ | 10 | MeOH | 23–35 | 87/13 | |
| 5 | NaBH$_4$ | 10 | MeOH | −10 | 93/7 | |
| 5 | NaBH$_4$ | 2.5 | H$_2$O 7, MeOH 3 | −10 | 94.5/5.5 | |
| 5 | NaBH$_4$ | 2.5 | H$_2$O 7, MeOH 3 | −10 | 98.5/1.5 | 2.5 mmol H$_3$PO$_4$ |

We claim:

1. A process for a stereoselective reduction of a 4-piperidone compound of the formula,

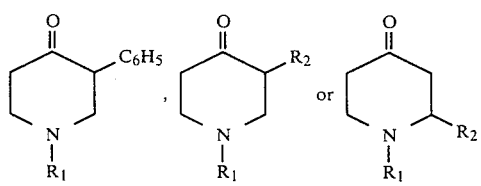

where $R_1$ is hydrogen, loweralkyl or benzyl and $R_2$ is methyl or ethyl, to a di-equatorial isomer of the corresponding 4-piperidinol, wherein said reduction is conducted by use of sodium borohydride at a temperature substantially lower than ambient temperature in a protic solvent medium in the presence of an inorganic acid or acidic salt thereof.

2. The process as defined in claim 1 wherein the protic solvent medium comprises an alcohol, water or a mixture thereof.

3. The process as defined in claim 2 wherein the protic solvent medium comprises methanol, water or a mixture thereof.

4. The process as defined in claim 1 wherein the reduction is conducted at a temperature below 0° C.

5. The process as defined in claim 2 wherein the reduction is conducted at a temperature below 0° C.

6. The process as defined in claim 3 wherein the reduction is conducted at a temperature below 0° C.

7. The process as defined in claim 6 wherein the molar amount of the inorganic acid in the reaction mixture is at least one half the molar amount of the 4-piperidone.

8. The process as defined in claim 7 wherein the inorganic acid is hydrochloric acid, hydrobromic acid, sulfuric acid, boric acid, phosphoric acid or a mixture thereof.

9. The process as defined in claim 1 wherein the 4-piperidone compound is

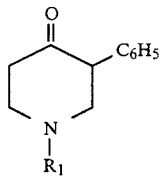

10. The process as defined in claim 9 wherein $R_1$ is methyl.

11. The process as defined in claim 8 wherein the 4-piperidone compound is

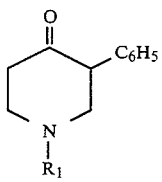

12. The process as defined in claim 11 wherein $R_1$ is methyl.

13. The process as defined in claim 1 wherein the 4-piperidone compound is

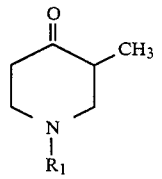

14. The process as defined in claim 13 wherein $R_1$ is methyl.

15. The process as defined in claim 8 wherein the 4-piperidone compound is

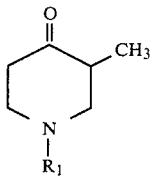

16. The process as defined in claim 15 wherein $R_1$ is methyl.

17. The process as defined in claim 1 wherein the 4-piperidone compound is

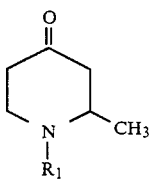

18. The process as defined in claim 17 wherein $R_1$ is methyl.

19. The process as defined in claim 8 wherein the 4-piperidone compound is

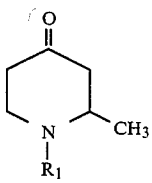

20. The process as defined in claim 19 wherein $R_1$ is methyl.

* * * * *